United States Patent [19]

Padros-Fradera

[11] Patent Number: 5,752,831
[45] Date of Patent: May 19, 1998

[54] DENTAL IMPLANT REPLICA

[76] Inventor: Alejandro Padros-Fradera, 310 Calle Balmes, 08006 Barcelona, Spain

[21] Appl. No.: 684,493

[22] Filed: Jul. 19, 1996

Related U.S. Application Data

[63] Continuation of Ser. No. 268,817, Jun. 30, 1994, abandoned.
[51] Int. Cl.$^6$ .................. A61C 8/00; A61C 19/00
[52] U.S. Cl. .................. 433/173; 433/74
[58] Field of Search .................. 433/74, 172, 173, 433/174, 175, 176, 214

[56] References Cited

U.S. PATENT DOCUMENTS

| | | | |
|---|---|---|---|
| 1,780,117 | 10/1930 | Craigo | 433/74 |
| 4,205,443 | 6/1980 | Weissman | 433/74 |
| 4,321,036 | 3/1982 | Weissman | 433/74 |
| 4,363,625 | 12/1982 | Der Aranessian | 433/74 |
| 4,941,827 | 7/1990 | Mack | 433/74 |
| 5,004,420 | 4/1991 | Soderberg | 433/172 |
| 5,108,288 | 4/1992 | Perry | 433/173 |
| 5,125,841 | 6/1992 | Carlsson et al. | 433/172 |
| 5,133,660 | 7/1992 | Fenick | 433/173 |
| 5,152,687 | 10/1992 | Amino | 433/173 |
| 5,234,339 | 8/1993 | Grigreit | 433/172 |
| 5,259,759 | 11/1993 | Jorneus et al. | 433/173 |
| 5,334,024 | 8/1994 | Niznick | 433/172 |

Primary Examiner—Nicholas D. Lucchesi
Attorney, Agent, or Firm—Michael J. Striker

[57] ABSTRACT

A dental implant replica fixable to models made of scagliola has an element adapted to carry a wax prosthesis, a fixed part fixable in a scagliola model to remain an integral part of the scagliola model, and a removably mountable part which is removably mountable on the fixed part and carries the element.

1 Claim, 2 Drawing Sheets

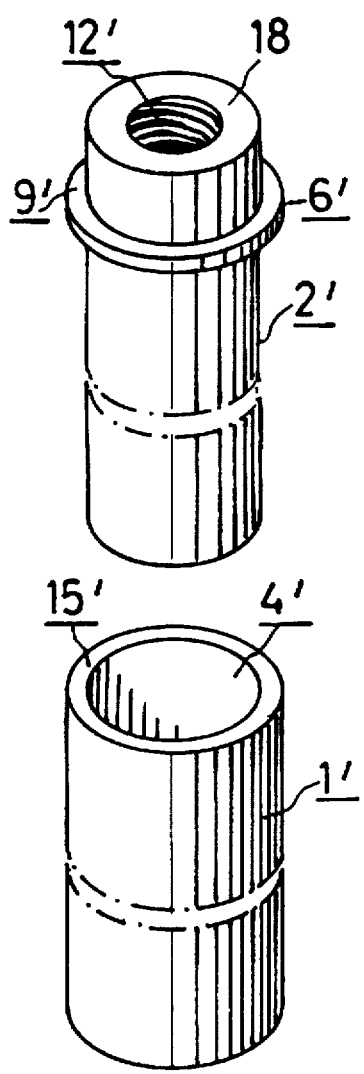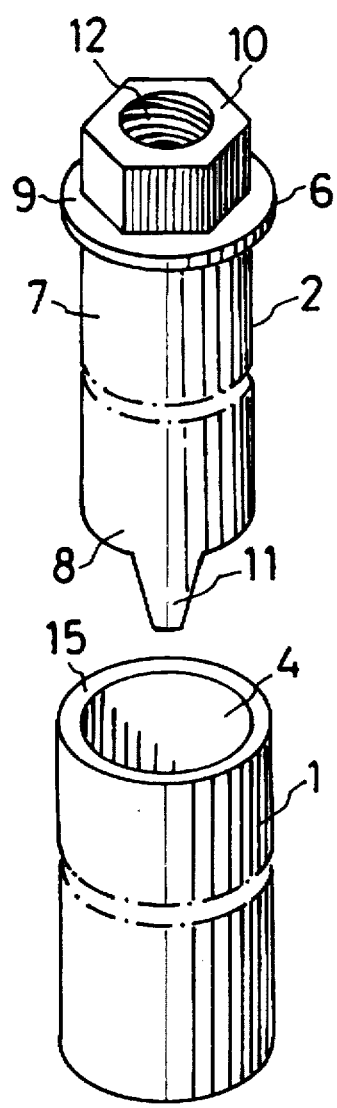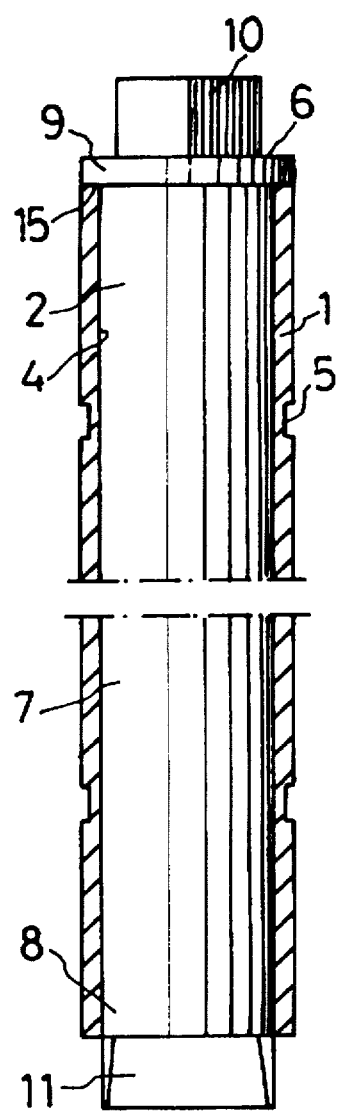

DENTAL IMPLANT REPLICA

This application is a continuation of Ser. No. 08/268,817, filed Jun. 30, 1994, now abandoned.

BACKGROUND OF THE INVENTION

The present invention deals with a dental implant replica which can be fixed to a dental model and has a copy of a pre-prosthesis collar of a dental implant or a copy of the implant itself for fitting dental prosthesis.

Known dental prostheses are obtained using a wax model or mold which is formed on a copy generally made of scagliola, of the patient's teeth. When a prosthesis is made on a dental implant, the wax mold is usually made on a calcinable collar, preferably of a plastic material, which fits onto the exact copy of the pre-prosthetic collar of the dental implant or onto the exact copy of the dental implant itself. Once the dental prosthesis has been made in metal from the wax mold, it can be fitted to the dental implant.

It is common practice for such replica or exact copy of the pre-prosthetic collar and/or the dental implant to be immovably fixed to the scagliola model of the patient's teeth. Therefore the wax mold of the dental prosthesis is made directly on the dental model itself in order to prevent any angular or linear movement during the formation of the wax mold which could affect the subsequent fitting of the prosthesis onto the dental implant arranged in the maxilla of the patient.

The main drawback of this technique for making the wax mold of a dental prosthesis is the fact that while the wax mold is being made it cannot be removed from the dental model to which the exact copy of the pre-prosthetic collar and/or of the implant is fixed. As a result of the operator making the wax mold has to work in difficult conditions leading to long execution times and therefore a corresponding increase in costs.

SUMMARY OF THE INVENTION

Accordingly, it is an object of the present invention to provide a dental implant replica which avoids the disadvantages of the prior art.

In keeping with these objects and with others which will become apparent hereinafter, one feature of the present invention resides, briefly stated, in a dental implant replica which has a fixed part to formed to remain an integral part of the scagliola model, and a removably mountable part which carries the pre-prosthetic head or the head of the implant.

When the dental implant replica is designed in accordance with the present invention, it has a new structure and type of operation and enables the wax mold of the dental prosthesis to be removed from the dental model made of scagliola and refitted as many times as necessary for its formation, without the need to use any tools.

The operator can work in total comfort and the time required to make the wax mold of the dental prosthesis is considerably reduced.

In accordance with another new feature of the invention the fixed part is formed as a hollow sleeve provided with a hole with an internal shape coinciding with an internal shape of a section of the removably mountable part. The removably mountable part is therefore adapted to be inserted tightly into the hole of the fixed part.

In accordance with still another feature of the present invention, the fixed part and the removably mountable part are provided with complementary means for insuring their correct longitudinal and angular positioning relative to one another.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a perspective view of a removably mountable part of a dental implant replica in accordance with the present invention;

FIG. 2 is a perspective view of a fixed part of the inventive dental implant replica;

FIG. 3 is a partially sectioned view of the fixed part and removably mountable part of the replica joined together;

FIGS. 7 and 8 are perspective views of a second embodiment of the fixed part and the removably mountable part of the replica in accordance with the present invention.

DESCRIPTION OF THE PREFERRED EMBODIMENTS

Figure 4:
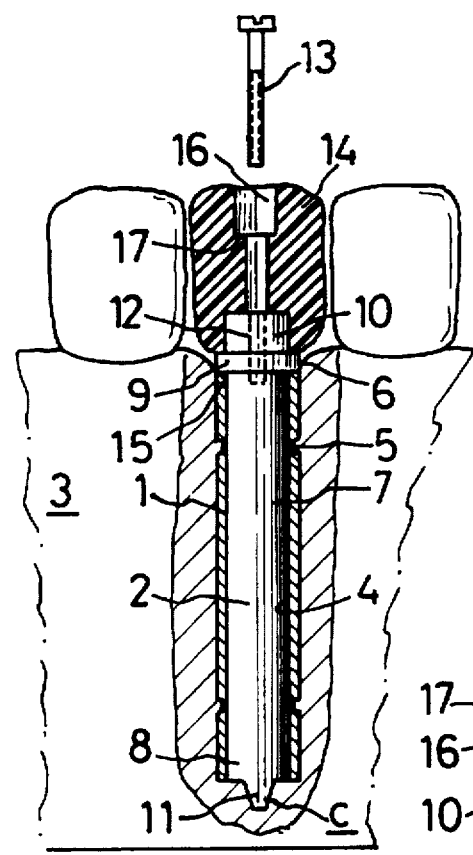
FIGS. 4, 5 and 6 are partially sectioned views of the replace showing the operation of the replica fitted to a dental model.
Figure 5:
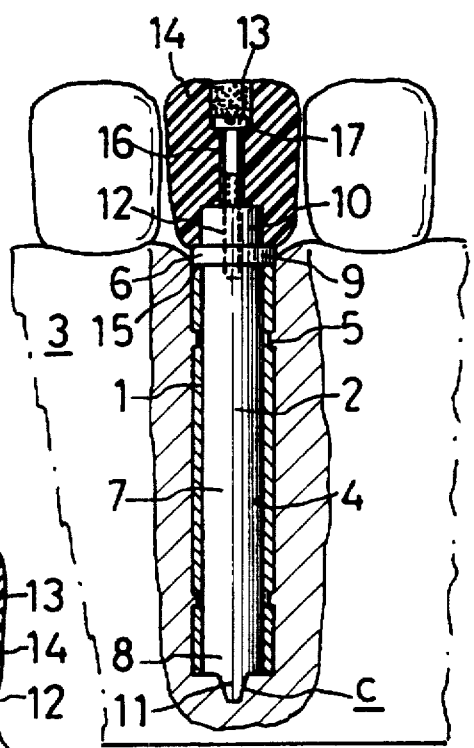
Figure 6:
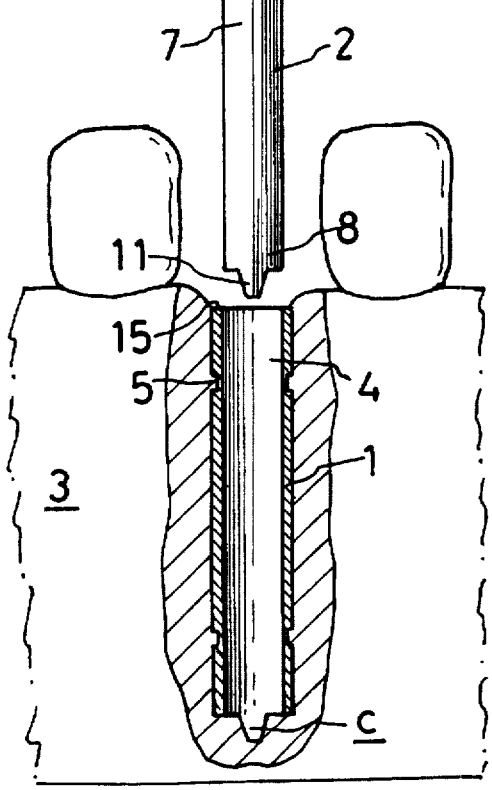

A dental implant replica in accordance with the present invention as shown in FIGS. 1–6 has a fixed part which is identified as a whole with reference numeral 1 and illustrated in FIG. 2, and a removably mountable part which is identified as a whole with reference numeral 2 and illustrated in FIG. 1. In the dental implant replica of the present invention the fixed part 1 and the removably mountable part 2 can be fixed together as shown in FIG. 3, and also the dental implant replica can be fixed to a dental model 3 made of scagliola which is a reproduction of the patient's teeth as shown in FIGS. 4, 5 and 6.

The fixed part 1 is substantially hollow cylindrical and formed as a sleeve. It is provided with an axial through hole 4 which has a size such that the removably mountable part 3 fits tightly inside it.

Externally, the fixed part 1 is provided with two peripheral grooves 5 for fixing the position of the fixed part 1 in the dental model 3. When the fixed part 1 is introduced into the dental model 3, the scagliola of the model occupies the peripheral grooves 5. Thereby once the dental model 3 has dried the fixed part 1 cannot be extracted from the bulk of the dental model 3 under normal conditions of use, so as to ensure that it is correctly positioned.

The removably mountable part 2 has a generally cylindrical shape. It is includes an out section 6, a central section 7, and an inner section 8.

The outer section 6 of the removably mountable part 2 has an axial enlargement 9 joined to a prismatic coaxial extension 10. The extension 10 is a copy of a pre-prosthetic collar of a dental implant which is not shown in the drawings. The central section 7 is cylindrical and has an outer diameter corresponding substantially to the inner diameter of the axial hole 4 of the fixed part 1. The inner section 8 is preferably provided with a central positioning extension 11 with a length appreciably equal to the diameter of the central section 7 and a trapezoidal cross-section. The extension 11 substantially corresponds to a shape of the tip of a screwdriver.

The prismatic coaxial extension 10 is provided with a threaded hole 12 which extends downwardly below the coaxial enlargement 9. The threaded hole 12 is adapted for receiving a bolt 13 for fixing the wax model 14 of the dental prosthesis to the removably mountable part 2.

The outer diameter of the coaxial enlargement 9 substantially corresponds to the outer diameter of the fixed part 1. The central section 7 and the inner section 8 can slide tightly through the fixed part 1, and the sliding movement is limited by the action of the coaxial enlargement 9 which acts as a stop against the front edge of the fixed part 1.

When the dental model 3 made of scagliola is in a plastic state, the fitting of the removably mountable part 2 into the fixed part until the coaxial enlargement 9 acts as a stop against the external edge 15, causes the positioning extension 11 of the removably mountable part to enter the bulk of the dental model 3. Thereby in the bulk a hole c is defined which corresponds in size and shape to the extension 11. Therefore once the dental model 3 has dried and the removably mountable part 2 is fully inserted into the fixed part, both parts 1 and 2 maintain the position relative to one another.

The prismatic coaxial extension 10 which forms the head of the implant itself is incorporated into the wax mold 14 initially modeled on calcinable plastic. The hole 16 and the intermediate step 17 are defined in the wax mold 14. The bolt 13 is placed inside the hole 16 and screwed into the hole 12 of the prismatic coaxial extension 10. Thereby the wax mold 14 is firmly secured to the removably mountable part 2 of the dental implant replica of the present invention. Therefore the removably mountable part 2 and as a result also the wax mold 14 can be fitted into and removed from the fixed part 1 as many times as necessary while the wax mold is formed.

A second embodiment of the dental implant replica in accordance with the present invention is shown in FIGS. 7 and 8. The dental implant replica of this embodiment has a fixed part 1' which corresponds to the fixed part 1 of the embodiment shown in FIGS. 1–6, and a removably mountable part 2'. The removably mountable part 2' has an outer section 6' with a coaxially enlargement 9' and a generally cylindrical coaxial extension 18. The coaxial extension 18 forms the head of the implant itself and is provided with a threaded hole 12'.

The second embodiment shown in FIGS. 7 and 8 differs from the first embodiment shown in FIGS. 1–6 in that, when the fixed part 1' is fitted into the dental model 3, the removably mountable 2' can be fitted in any angular position. In other words, once both the fixed part 1' and the removably mountable part 2' have been fitted, the removably mountable part can be rotated about its longitudinal axis.

It will be understood that each of the elements described above, or two or more together, may also find a useful application in other types of constructions differing from the types described above.

While the invention has been illustrated and described as embodied in a dental implant replica, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

I claim:

1. A dental implant replica fixable to models made of scagliola, comprising a removably mountable part having an outer section, a central section and an inner section with a central positioning extension, said removably mountable part being provided with a threaded hole for receiving a bolt for fixing a scagliola model; a fixed part adapted to be fixed to a scagliola model, said fixed part having an axial hole with an inner diameter corresponding to an outer diameter of said central section of said removably mountable part so that said central section with said central positioning extension is insertable and extends through said axial hole of said fixed part, said outer section of said removably mountable part having a coaxial enlargement with an outer diameter substantially corresponding to said outer diameter of said fixed part so that when said central section and said inner section slide tightly through said axial hole of said fixed part, a sliding movement is limited by said coaxial enlargement which acts as a stop against a front edge of said fixed part; and a bolt screwable into said coaxial enlargement to firmly secure a scagliola model to said removably mountable part, said fixed part being provided with peripheral grooves for fixing a position of said fixed part in a dental model.

* * * * *